United States Patent
Lewis

(10) Patent No.: US 10,151,937 B2
(45) Date of Patent: *Dec. 11, 2018

(54) DIGITAL EYEWEAR

(71) Applicant: Percept Technologies Inc., Las Vegas, NV (US)

(72) Inventor: Scott W. Lewis, Las Vegas, NV (US)

(73) Assignee: Percept Technologies Inc, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,814

(22) Filed: Jan. 22, 2016

(65) Prior Publication Data

US 2016/0139435 A1  May 19, 2016

Related U.S. Application Data

(60) Continuation of application No. 14/660,497, filed on Mar. 17, 2015, now Pat. No. 9,244,293, which is a continuation of application No. 13/739,929, filed on Jan. 11, 2013, now Pat. No. 9,010,929, which is a continuation of application No. 13/078,589, filed on Apr. 1, 2011, now Pat. No. 8,353,594, which is a continuation of application No. 12/621,423, filed on Nov. 18, 2009, now Pat. No. 7,918,556, which is a continuation of application No. 12/029,068, filed on Feb. 11, 2008, now Pat. No. 7,758,185, which is a (Continued)

(51) Int. Cl.
*G02C 11/00* (2006.01)
*G09G 3/00* (2006.01)
*G02B 27/00* (2006.01)
*G02B 27/01* (2006.01)

(52) U.S. Cl.
CPC .......... *G02C 11/10* (2013.01); *G02B 27/0093* (2013.01); *G02B 27/0172* (2013.01); *G09G 3/00* (2013.01); *G02B 2027/0132* (2013.01); *G02B 2027/0138* (2013.01); *G02B 2027/0178* (2013.01)

(58) Field of Classification Search
CPC .......... G02C 11/00; G02C 11/06; G02C 11/10
USPC .............. 351/158, 159.73; 359/13, 630–633; 385/8; 345/7–9

See application file for complete search history.

(56) References Cited

U.S. PATENT DOCUMENTS 6,099,124 A * 8/2000 Hidaji ................. A61B 3/113
351/159.39
6,222,508 B1 * 4/2001 Alvelda ............... G02B 27/017
345/2.1

(Continued)

*Primary Examiner* — Darryl J Collins

(57) ABSTRACT

Improved eyewear is disclosed. The eyewear comprises a frame member and a lens. The eyewear also includes circuitry within the frame member for enhancing the use of the eyewear. A system and method in accordance with the present invention is directed to a variety of ways to enhance the use of eyeglasses. They are: (1) media focals, that is, utilizing the eyewear for its intended purpose and enhancing that use by using imaging techniques to improve the vision of the user; (2) telecommunications enhancements that allow the eyeglasses to be integrated with telecommunication devices such as cell phones or the like; and (3) entertainment enhancements that allow the eyewear to be integrated with devices such as MP3 players, radios, or the like.

22 Claims, 6 Drawing Sheets

Related U.S. Application Data division of application No. 11/245,756, filed on Oct. 7, 2005, now abandoned.

(56) References Cited

U.S. PATENT DOCUMENTS

| | | | | |
|---|---|---|---|---|
| 6,231,183 B1 * | 5/2001 | Dillon | ............... | G02C 7/02 |
| | | | | 351/159.6 |
| 6,307,526 B1 * | 10/2001 | Mann | ............... | G02B 27/017 |
| | | | | 345/7 |
| 6,608,615 B1 * | 8/2003 | Martins | ............... | G06F 3/013 |
| | | | | 345/156 |
| 7,677,734 B2 * | 3/2010 | Wallace | ............... | A61B 5/055 |
| | | | | 345/8 |
| 7,738,179 B2 * | 6/2010 | Nishi | ............... | G02B 27/0025 |
| | | | | 345/8 |
| 2006/0023158 A1 * | 2/2006 | Howell | ............... | G02C 11/10 |
| | | | | 351/41 |

* cited by examiner

102'

300

400

DIGITAL EYEWEAR

CROSS-REFERENCE TO RELATED APPLICATION

Under 35 USC § 120, this application is a continuation application and claims the benefit of priority to U.S. patent application Ser. No. 14/660,497, filed on Mar. 17, 2015, entitled "DIGITAL EYEWEAR", which is a continuation application and claims the benefit of priority to U.S. patent application Ser. No. 13/739,929, filed on Jan. 11, 2013, entitled "DIGITAL EYEWEAR", now U.S. Pat. No. 9,010,929, issued on Apr. 21, 2015, which is a continuation application and claims the benefit of priority to U.S. patent application Ser. No. 13/078,589, filed on Apr. 1, 2011, entitled "DIGITAL EYEWEAR", now U.S. Pat. No. 8,353,594, issued on Jan. 15, 2013, which is a continuation of U.S. patent application Ser. No. 12/621,423, filed on Nov. 18, 2009, entitled "DIGITAL EYEWEAR", now U.S. Pat. No. 7,918,556, issued on Apr. 5, 2011, which is a continuation of U.S. patent application Ser. No. 12/029,068, filed Feb. 11, 2008, entitled "DIGITAL EYEWEAR", now U.S. Pat. No. 7,758,185, issued on Jul. 20, 2010, which is a divisional application of U.S. patent application Ser. No. 11/245,756, filed Oct. 7, 2005, entitled "DIGITAL EYEWEAR", all of which are incorporated herein by reference.

FIELD OF THE INVENTION

The present invention relates generally to eyewear and more particularly to eyewear that includes additional functionality.

BACKGROUND OF THE INVENTION

Eyewear is utilized for a variety of purposes. Eyewear is used for improving one's vision for reading glasses and to protect one's vision. Oftentimes protective goggles are used to protect eyes within dangerous areas. It is desirable to add additional functionality to glasses. This functionality can include a variety of forms, which are electronic, mechanical, aesthetic, etc. Accordingly, it is always desired to provide additional functionality to eyewear. What is desired is a system and method which will increase the functionality of glasses beyond their normal use while still maintaining them for their primary uses. The present invention addresses such a need.

SUMMARY OF THE INVENTION

Improved eyewear is disclosed. The eyewear comprises a frame member and a lens. The eyewear also includes circuitry within the frame member for enhancing the use of the eyewear.

A system and method in accordance with the present invention is directed to a variety of ways to enhance the use of eyeglasses. They are:

(1) Media focals, that is, utilizing the eyewear for its intended purpose and enhancing that use by using imaging techniques to improve the vision of the user.

(2) Telecommunications enhancements that allow the eyeglasses to be integrated with telecommunication devices such as cell phones or the like.

(3) Entertainment enhancements that allow the eyewear to be integrated with devices such as MP3 players, radios, or the like.

DETAILED DESCRIPTION

The present invention relates generally to eyewear and more particularly to eyewear that includes additional functionality. The following description is presented to enable one of ordinary skill in the art to make and use the invention and is provided in the context of a patent application and its requirements. Various modifications to the preferred embodiments and the generic principles and features described herein will be readily apparent to those skilled in the art. Thus, the present invention is not intended to be limited to the embodiments shown, but is to be accorded the widest scope consistent with the principles and features described herein.

A system and method in accordance with the present invention is directed to a variety of ways to enhance the use of eyeglasses. There are three areas of eyeglass enhancement which are identified in the present application. They are:

(1) Media focals that is, utilizing the eyewear for its intended purpose and enhancing that use by using imaging techniques to improve the vision of the user.

(2) Telecommunications enhancements that allow the eyeglasses to be integrated with telecommunication devices such as cell phones or the like.

(3) Entertainment enhancements that allow the eyewear to be integrated with devices such as MP3 players, radios, or the like.

Finally, these features can be utilized together to provide a user with all of the above-enhanced features. To describe the features of the present invention in more detail refer now to the following description in conjunction with the accompanying figures.

1. Media Focals 100

Figure 1:
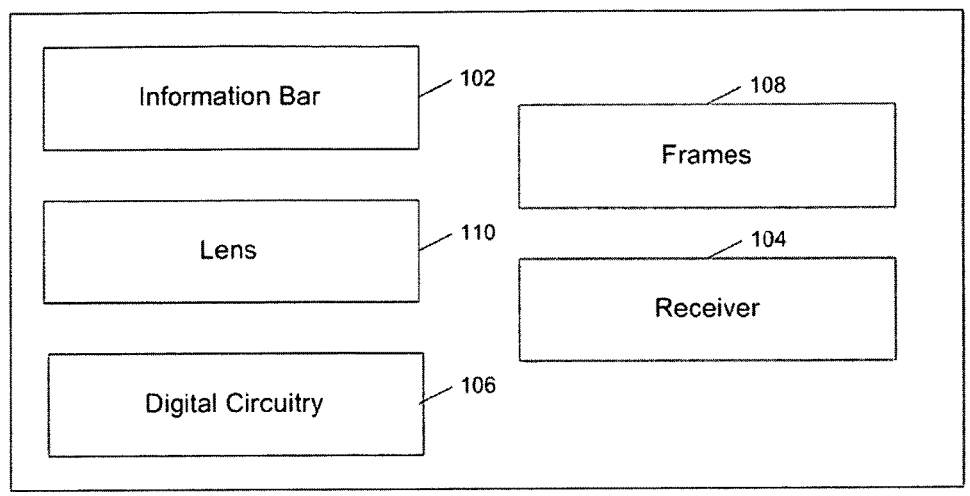
FIG. 1 is a diagram that illustrates Media focals.

FIG. 1 is a diagram that illustrates Media focals 100. Media focals 100 comprises an information bar 102, receiver 104, digital circuitry 106, frames 108 and lens 110. Media focals 100 allow for enhancing the eyewear for its primary purpose, for example, a digital camera could be placed within the eyewear to allow for seeing certain of these images. For example, the circuitry 106 for the media focals 100 could be placed within the frame 108 of the eyewear. The lens 110 could have a totally reflective surface, or a partially reflective surface using LCDs or the like. In effect the eyewear could look like see-through glasses, but through the use of the circuitry 106 within the eyewear it is actually a media focal. Additionally, the eyewear could incorporate a camera to project the user onto a second lens to achieve a see-through effect.

In a preferred embodiment, an information bar 102 is provided across a portion of the eyewear which is visible to the user. This information bar 102 is used to convey a variety of types of information.

Figure 2:
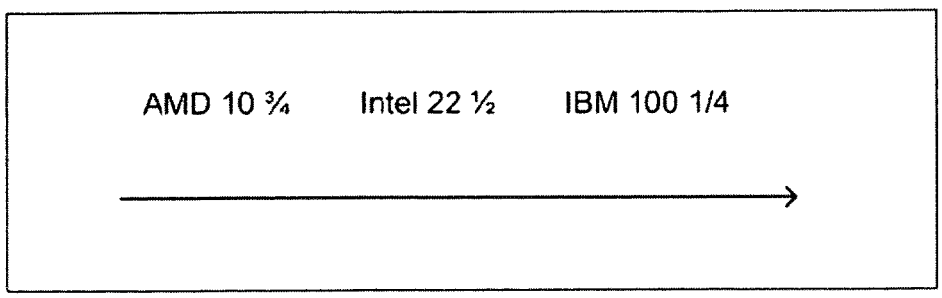
FIG. 2 illustrates an information bar on media focal eyewear.

FIG. 2 comprises an information bar 102' on media focal eyewear. The information bar 102' can be a stock ticker scrolling across the top portion of the eyewear, as is shown in FIG. 2. Although the information bar 102' is shown displaying a stock ticker, other kinds of information such as song titles, lyrics and the like could be displayed in the information bar. This information bar is referred to as E-focals. This information might be provided from a digital receiver through an FM station, through a cellular wireless device, or an MP3 player. Additional functionality of the E-focal will be described with more detail with respect to the cell phone enhancements as well as the music player enhancements.

One of the key features of the media focals 100 is the use of the media focals to enhance the primary function of the user, that is, being able to more accurately and clearly see the objects. In such an environment, for example, it is possible to have a zoom feature circuit to allow for the use of the eyewear as binoculars. This would allow for the user to see objects more closely based on certain activities of the user. For example, there may be eye or pressure sensors on the eyewear that will activate the binocular circuitry in the glasses which could receive visual data through a camera, CCD receiver of the like.

In the preferred embodiment, the circuitry 106 would be located somewhere in the frame of the glasses to provide this functionality and as circuits became smaller and devices became smaller it would be easier and easier to embed the circuitry that is well known for use for such functions directly within the device. The circuitry 106 in the device could be, for example, eye sensors which could be pressure sensors, capacitive sensors or some other type of sensor for allowing the eyes to direct the activities. Eye movement sensors, for example, could be used to activate and control the binocular glasses. Similarly, a digital camera could be put on the glasses that would allow the same kinds of technology to take pictures by the person directly.

In a similar vein, the glasses could be used as a normal corrective lens glass utilizing the digital imagery, so that, for example, a user has a certain prescription that they use with their normal prescription glasses to view an object clearly. As the user's eyes change, it would be possible that an optometrist could download the new prescription to the eyewear such that a digital transformation of the image information is provided which is compatible with the new prescription.

Also, in a preferred embodiment a method for sensing and controlling the digital media could be implemented in a variety of ways. For example, an activity of the eye itself would control the activity of the media focal. So, for example, if the idea was to zoom the image, the eye would blink twice. It would also be possible to detect facial and eye movements (squinting, for example), as well as changes in the pupil and iris.

In a further embodiment, it would be possible for the eyeglasses in accordance with the present invention to function within a client/server model or Bluetooth (wi fi) model. Utilization of the client/server model and Bluetooth wifi would make possible, for example, the display of live news or special reports (such as financial reports) from the Internet or similar sources on the eyeglasses. This would also allow for portions of circuitry to be located remotely such that less circuitry in the eyewear is required.

The eyewear could also include a logo, for example, law enforcement officers could have their glasses emblazoned with "Police", "Sheriff", "MP", etc.; young people could have their eyeglasses emblazoned with words and images that reflected their favorite performers, etc.; sports teams could offer the eyeglasses at discount with team monograms, etc. They could also be purchased by companies, emblazoned with the company logos, and given out as retirement gifts, etc.

2. Music Environment

Figure 3:
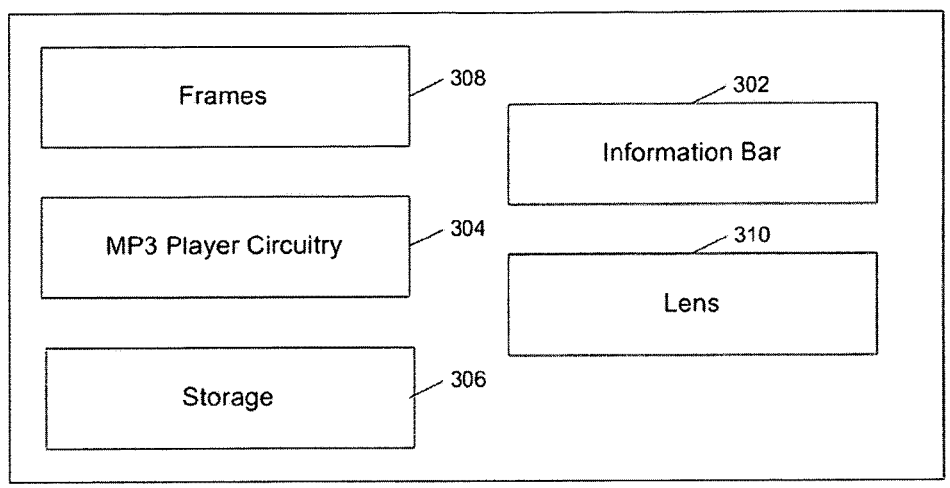
FIG. 3 is a block diagram of the features of eyewear that are utilized in a music environment such as an MP3 player.
Figure 3A:
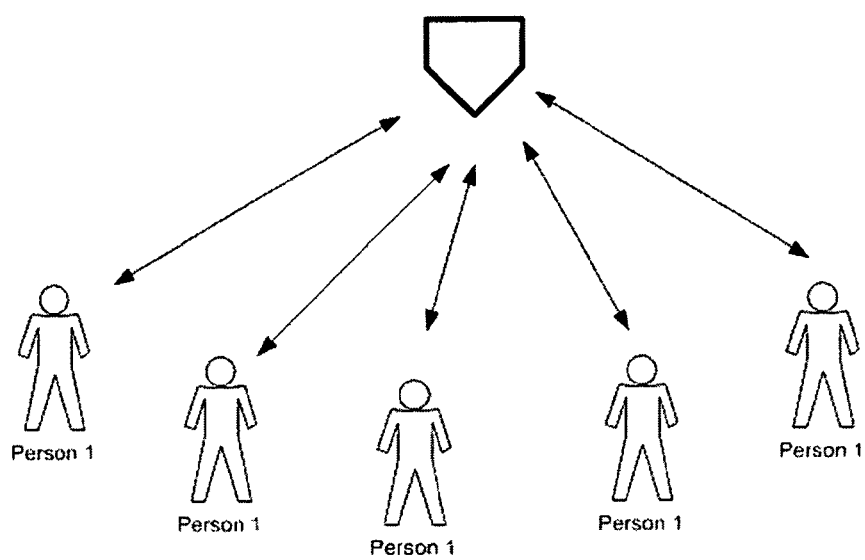
FIG. 3a illustrates a plurality of MP3 player eyewear users in a karaoke performance.

FIG. 3 is a block diagram of eyewear 300 that is utilized in a music environment such as an MP3 player. FIG. 3 comprises eyewear 300, an information bar 302, MP3 player circuitry 304, storage 306, frames 308, and one or a plurality of lenses 310. Another environment as has been above described is the music environment. What would be desirable would be to provide music glasses in which an MP3 player on an IPod or the like is incorporated in the eyewear, either in a wired or wireless environment. Through the use of this type of system, a plurality of users could be networked via an MP3 player type environment within a hotspot, or the like, which would allow one to have downloads of whatever music is required through the eyeglasses. The system could allow for downloadable music which could be selected via scrolling and the like through voice recognition systems.

By connecting to a client-server network or Bluetooth wifi installation, for example, the eyeglasses could link to a multimedia network, authorize downloading and billing for selected music. By this means, access to a plurality of libraries for music selections could be provided.

It would also be possible to provide access to streaming audio media. Also, access can be provided to multimedia libraries, etc., via the client/server model.

Information could be received via a digital client/server model enabled to work with iPods or MP3 players. Similarly, bluetooth wireless technology could be utilized to provide access to music and live audio sources.

The eyewear could also be utilized in conjunction with wireless technology to allow a user or a plurality of users to participate simultaneously in single or group karaoke singing. The eyewear could be used specifically to display the lyrics of a song, melody, notes, name of the song or other associated references.

It would also be possible to receive and listen to AM or FM radio signals, via an AM/FM radio tuner connected to the eyewear hardware.

In this type of environment, the headphones can be either digital or analog. The user doesn't need to have 10,000 songs, for example. They can come enrolled in an in-song virtual network library upon entering a hotspot. Therefore, the local storage 306 could be limited. In addition, this would provide location identity information for one who is using the network. The songs can be streamed as well as downloaded. The songs could be purchase using the eyewear. The system could be scaleable; depending upon what kind of device was being used.

3. Telecommunications Environment

Figure 4:
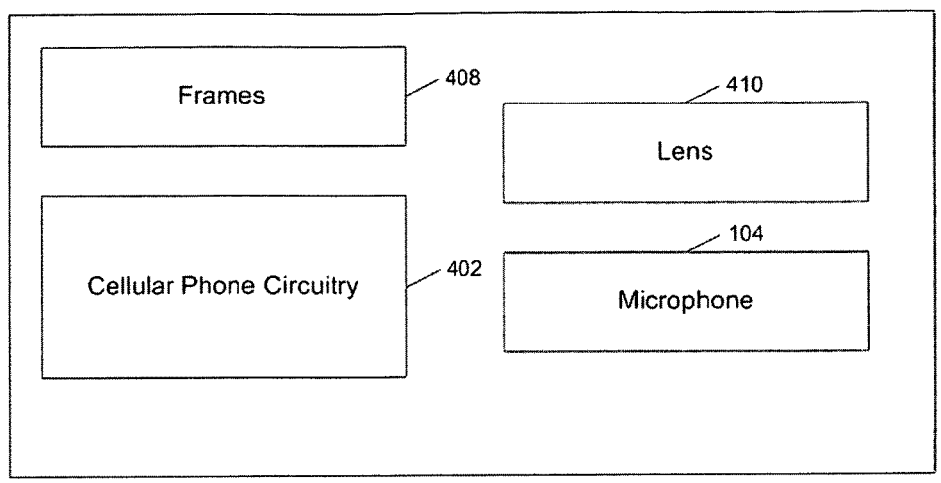
FIG. 4 is a block diagram that illustrates eyewear that is utilized as a cell phone.
Figure 5:
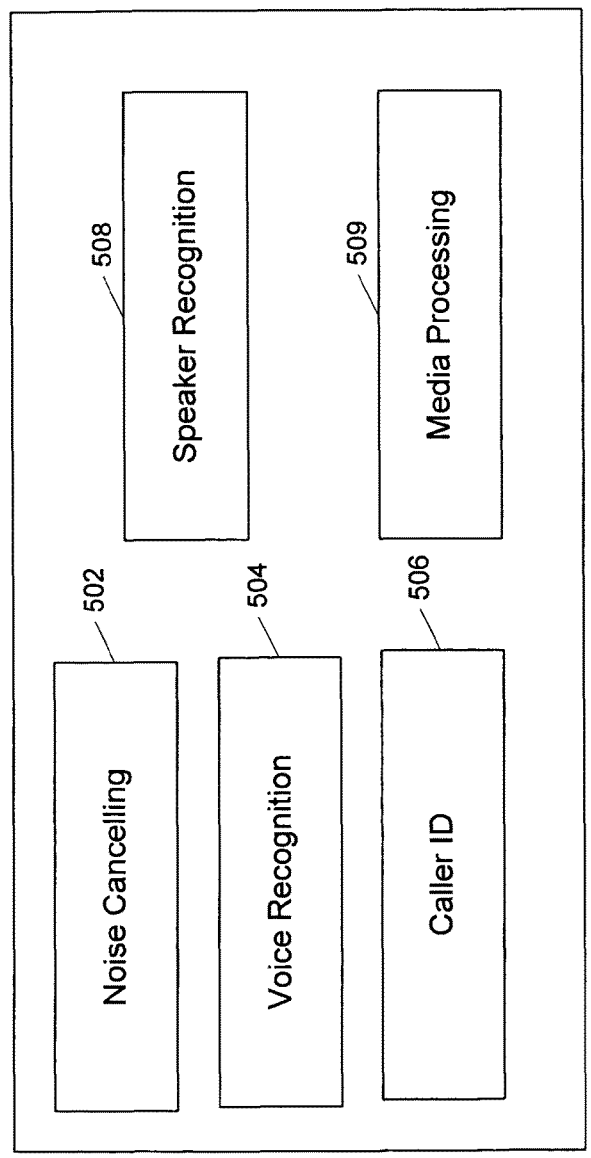
FIG. 5 is a block diagram that illustrates the cellular phone circuitry of FIG. 4.

FIG. 4 is a block diagram that illustrates eyewear that is utilized as a cell phone 400. FIG. 4 comprises cellular phone circuitry 402, a microphone 104, frames 408 and one or a plurality of lenses 410. The cell phone eyewear 400 could be implemented utilizing digital telephone technology. Circuitry 402 within the eyewear could be utilized to allow a telephone number or other visual information such as that provided by multimedia messaging services to be displayed on the lens 410 of the eyewear as shown in FIG. 3. FIG. 5 is a block diagram that illustrates the cellular phone circuitry of FIG. 4. FIG. 5 comprises noise cancelling circuitry 502, voice recognition circuitry 504, caller ID circuitry 506 and speaker recognition circuitry 508 and media processing circuits 509. The telephone number could be activated via the digital circuitry 402 as part of the media focals 100. In addition, the circuitry could be made truly digital via a digital signal processor which is coupled to a camera otherwise in the environment. The above system would allow for voice recording through use of a microphone 104 and would allow for voice recognition through use of the voice recognition circuitry 504, which would allow for signal conditioning on the cell phone in a variety of ways.

The cell phone environment 402 provides a plurality of areas for improvement utilizing existing technologies. Firstly, one of the major annoyances in cell phone use is that the users have to speak in a loud manner because of background noise and the like. There are a variety of reasons for this problem including the placement of the microphone of the cell phone relative to the speaker's mouth, due to the aforementioned background noise, and other issues. By placing the microphone 104 strategically on the eyewear such as near the noise or mouth the user will not have to speak as loudly. The microphone could also be located in flip down microphones. In addition noise canceling circuitry 502 could be utilized to remove the background noise. The microphone capability would include the advantage of utilizing noise rejection techniques. Buttons located on the eyewear can be utilized to control features thereon. Finally, the microphone 104 could utilize whisper technology such that the speaker will not have to speak as loudly.

The eyewear would in a preferred embodiment include voice recognition circuitry 504 and caller ID circuitry 506. The conventionality for hearing and talking in a preferred embodiment would be located in ear and nose pad portions of glasses. Referring back to FIG. 3, the electronics for the cell phone in a preferred embodiment would be within the frame 308 of the eyewear. In addition the eyewear would include a fully integrated information bar 302. Finally, a speaker recognition algorithm 508 as shown in FIG. 5 would allow only the voice of the user to be recognized and the background noise would be cancelled. Accordingly, the unique characteristics of the speaker are provided via an audible model.

This can performed utilizing a variety of methods. For example analyzing the voice of the user and combining the analysis with noise cancellation. In another example the user can talk softly and cancel noise and a directional microphone is used which takes advantage of device location.

Similar to the media focal and MP3 player environments, a digital client/server or Bluetooth/wifi model could be adapted to link the eyewear to external communication equipment. Such equipment could include digital cell phones, PDAs or wifi enabled PCs or other devices. Such an embodiment could enable review of voicemail, screen viewed emails, text to speech audio email conversions, multimedia messaging services, and other data sources.

Wireless or Bluetooth interconnection could also make possible VOIP glasses to be utilized instead of a cell phone. Other features enabled by a wireless link could link the eyeware to MP3 devices, an iPod, a printer, wireless/wired TV, coupons, and the like. Also "FDA glasses" could provide built in a time display, alarm calendar, interfacing with PCs or network sources, a speaker and the like.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for providing eyewear comprising:
providing a frame member;
providing a binocular mechanism;
providing circuitry within the frame member and coupled to the binocular mechanism for enhancing the use of the eyewear; and
providing an eye sensor coupled to the frame member, the eye sensor activating the circuitry responsive to an eye motion of a user.

2. The method of claim 1
further includes providing pressure sensors within the eyewear wherein the pressure sensors activate the binocular mechanism.

3. The method of claim 2
further includes providing a receiver within the eyewear wherein the receiver receives visual data.

4. The method of claim 1,
wherein the circuitry provides an information bar across a field of view for the user.

5. The method of claim 1,
including steps of providing a lens;
wherein the lens is reflective.

6. The method of claim 1,
including steps of providing a lens;
wherein the lens is partially reflective.

7. The method of claim 1,
wherein the circuitry provides any of a cell phone, media focals, and an MP3 player.

8. The method of claim 1,
including steps of providing a lens;
wherein an information bar is provided on the lens.

9. The method of claim 1,
wherein the eyewear can be utilized in a client server system to allow for the display of certain information.

10. The method of claim 1,
including steps of providing a lens;
wherein a logo is placed on a front surface of the lens.

11. The method of claim 1,
including steps of providing a lens;
wherein the eyewear incorporates a camera to project a reciprocal display using a second lens.

12. The method of claim 1,
wherein the eyewear includes a pushbutton system for control.

13. A method as in claim 1,
wherein the eye motion includes one or more of:
an eye blink, an eye squint, or a change in the pupil or iris;
a facial movement of the user other than head movement.

14. A method for providing eyewear comprising:
providing a frame member;
providing a lens, wherein an information bar is provided on the lens;
providing circuitry within the frame member for enhancing the use of the eyewear; and
providing at least one motion or pressure sensor coupled to the frame member, an eye sensor coupled to the frame member, the eye sensor activating the circuitry responsive to activity of the eye itself of a user to directly control a function directed by the user the at least one motion or pressure sensor activating the circuitry responsive to one or more of:
an eye motion of the user; facial movements of the user other than head movement; or an eye blink, an eye squint, or a change in the pupil or iris.

15. The method of claim 14,
wherein the eyewear can be utilized in a client server system to allow for the display of certain information.

16. The method of claim 14,
wherein the eyewear includes a pushbutton system for control, the circuitry can provide any of texts, email; multimedia information; caller id.

17. A method for providing eyewear comprising:
providing a frame member;
providing a lens, wherein an information bar is provided on the lens;
wherein the lens has a set of integrated media enhancements, wherein information is provided on the lens, an eye sensor coupled to the frame member, the eye sensor activating the circuitry responsive to an eye motion of a user, and
providing circuitry within the frame member for enhancing the use of the eyewear; wherein the circuitry includes voice recognition when a speaker is recognized.

18. The method of claim 17,
wherein the eyewear can be utilized in a client server system to allow for the display of certain information within the field of view of a user.

19. The method of claim 17,
wherein the eyewear includes a pushbutton system for control.

20. The method of claim 17,
wherein the circuitry can provide any of texts, email; multimedia information; caller id.

21. The method of claim 17,
wherein the circuitry includes noise cancellation being utilized with the recognized speaker.

22. A method as in claim 17,
wherein the eye motion includes one or more of:
an eye blink, an eye squint, or a change in the pupil or iris;
a facial movement of the user other than head movement.

* * * * *